United States Patent
Lou et al.

(10) Patent No.: US 12,049,451 B2
(45) Date of Patent: Jul. 30, 2024

(54) HIGHLY EFFICIENT PROCESS FOR THE PREPARATION OF 4-FLUORO-1H-PYRAZOLE OR SALTS THEREOF

(71) Applicant: F.I.S.—Fabbrica Italiana Sintetici S.p.A., Montechhio Maggiore (IT)

(72) Inventors: Kexia Lou, Zhejiang (CN); Jian Dong, Zhejiang (CN)

(73) Assignee: F.I.S.—FABBRICA ITALIANA SINTETICI S.P.A., Montecchio Maggiore (IT)

( * ) Notice: Subject to any disclaimer, the term of this patent is extended or adjusted under 35 U.S.C. 154(b) by 0 days.

(21) Appl. No.: 18/160,323

(22) Filed: Jan. 27, 2023

(65) Prior Publication Data
US 2023/0242489 A1  Aug. 3, 2023

(30) Foreign Application Priority Data
Jan. 28, 2022 (EP) .................................. 22153889

(51) Int. Cl.
*C07D 231/16* (2006.01)
(52) U.S. Cl.
CPC ................... *C07D 231/16* (2013.01)
(58) Field of Classification Search
CPC .................................................. C07D 231/16
USPC ....................................................... 548/373.1
See application file for complete search history.

(56) References Cited

FOREIGN PATENT DOCUMENTS

| WO | 2013043624 A1 | 3/2013 |
| WO | 2017214634 A1 | 12/2017 |
| WO | 2021173731 A1 | 9/2021 |

OTHER PUBLICATIONS

Shi et al., "Reactions of β-fluorovinamidinium salt with bifunctional hetero nucleophiles. A new synthetic route to fluorinated heterocycles", Tetrahedron Letters, vol. 36, Issue 9, Feb. 27, 1995, pp. 1527-1530.
Sloop et al., "Microwave-Mediated Pyrazole Fluorinations Using Selectfluor", Heteroatom Chemistry, vol. 20, No. 6, Jan. 1, 2009, pp. 341-345.
Breen et al., "Synthesis of 4,4-Difluoro-1H-pyrazole Derivatives", Synlett 2015, vol. 26, No. 01, pp. 51-54, published online on Nov. 5, 2014.
German Version of Justus Liebigs Annalen Chemie, Reichardt, 975, (3), 470-483. (The year of publication is sufficiently earlier than the effective U.S. filing date so that the particular month of publication is not an issue).
English translation of Justus Liebigs Annalen Chemie, Reichardt, 975, (3), 470-483. (The year of publication is sufficiently earlier than the effective U.S. filing date so that the particular month of publication is not an issue).

*Primary Examiner* — Taofiq A Solola
(74) *Attorney, Agent, or Firm* — TAROLLI, SUNDHEIM, COVELL & TUMMINO L.L.P.

(57) ABSTRACT

Highly efficient process for the preparation of 4-Fluoro-1H-pyrazole or salts thereof by reaction of pyrazole with an electrophilic fluorinating reagent is disclosed.

13 Claims, No Drawings

HIGHLY EFFICIENT PROCESS FOR THE PREPARATION OF 4-FLUORO-1H-PYRAZOLE OR SALTS THEREOF

CROSS-REFERENCE TO RELATED APPLICATIONS

The present application claims priority to European Patent Application No. EP22153889.5 filed on 28 Jan. 2022. This document is hereby incorporated by reference in its entirety

TECHNICAL FIELD

The present invention concerns a small molecule, in particular 4-Fluoro-1H-pyrazole or salts thereof and a highly efficient process for its preparation.

4-Fluoro-1H-pyrazole or salts thereof is currently used as a starting material for the synthesis of many metal-organic compounds or organic small molecules, including active or potentially active pharmaceutical compounds.

BACKGROUND ART

The compound 4-Fluoro-1H-pyrazole or salts thereof, having the following chemical formula (I):

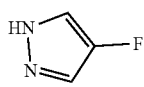
(I)

has also chemical name 4-Fluoropyrazole and CAS RN 35277-02-2.

4-Fluoro-1H-pyrazole, also named 4-Fluoropyrazole, is currently prepared by synthetic processes which includes many synthetic steps such as those disclosed in Example 28 of WO2013043624 wherein, starting from a compound bearing a fluorine atom, in three steps, whose the last is a cyclization by hydrazine, said compound is prepared.

A similar process was previously disclosed in Justus Liebigs Annalen Chemie (1975), (3), 470-483 wherein 4-Fluoro-1H-pyrazole is prepared by cyclization of 2-Fluoromalondialdehyde with hydrazine.

Shi, Xifeng et al. in Tetrahedron Letters (1995), 36(9), 1527-30 discloses a process for the preparation of 4-Fluoropyrazole starting from a trifluoroammonium alkenyl compound which, after reaction with diethylamine, is converted into the final compound by reaction with hydrazine.

Thus, by the exam of the literature, it appears clear that 4-Fluoro-1H-pyrazole is always prepared by cyclization of compounds bearing a Fluorine atom, wherein said cyclization is performed with hydrazine or salts thereof.

However, all said methods suffers from the drawbacks related to the lengths of the synthetic route of synthesis, i.e. many synthetic steps, and the use of hydrazine which is well known to be a cancerogenic substance.

The international application WO2017214634 discloses active pharmaceutical ingredients having the following formula:

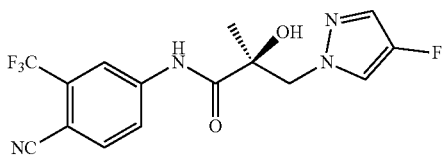 [SMILES: C[C@](O)(Cn1cc(F)cn1)C(=O)Nc1ccc(C#N)c(C(F)(F)F)c1]

and derivatives thereof comprising the 4-Fluoropyrazole moiety. In particular, the compound mentioned above as well as, the compounds described in WO2017214634 with the numbers 1007, 1017, 1020, 1022, 1023, 1024, 1029, 1041, 1046, all of them having 4-Fluoropyrazole moiety, are indicated to be Selective Androgen Receptor Degrader (SARS) Ligands.

The international application WO2021173731 discloses the compound of formula:

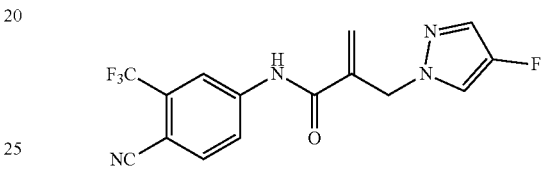

as well as other compounds indicated with number, 2, 9, 11, 12, 17, all of them having the 4-Fluoropyrazole moiety, are identified as being Selective Androgen Receptor Covalent Antagonist (SARCAS).

Therefore the compound 4-Fluoropyrazole prepared according to the process of the invention could be, for instance, useful in the supply chain involved in the preparation of above said SARS or SARCAS compounds.

SUMMARY OF INVENTION

The problem addressed by the present invention, in the light of the prior art processes described above, is therefore that of providing a process for the preparation of 4-Fluoro-1H-pyrazole or salts thereof which allows, at the same time:
  to avoid the use of hydrazine,
  to prepare said compound only with one chemical reaction starting from a chemical commodity, thus providing a direct and highly efficient process of preparation of 4-Fluoro-1H-pyrazole or salts thereof.

The process of the invention solves such a problem, since with only one chemical reaction, stating from Pyrazole, selectively provides 4-Fluoro-1H-pyrazole, without the use of hydrazine.

It is indeed clear that, starting from Pyrazole, other substances could be potentially produced by direct fluorination, such as the isomer 3-Fluoropyrazole or other impurities such as 3,4-Difluoropyrazole, therefore a clear potential issue related to the selectivity of the reaction always arises to the skilled person in the field of synthetic organic chemistry.

Nevertheless, the process of the invention also overcomes the potential selectivity problems providing a process that selectively and directly gives 4-Fluoro-1H-pyrazole or salts thereof starting from a chemical commodity such as Pyrazole.

As additional advantage, it would be desirable to avoid acid conditions since the presence of hydrofluoric acid, also in small amounts, is detrimental for the reactor still, because of the high corrosion caused by hydrofluoric acid. Therefore, according to an embodiment of the process of the invention, the reaction is carried out at a pH comprised in the range from 6.0 to 8.0.

Furthermore, since the process of the invention uses, for the first time, pyrazole for the preparation of 4-fluoropyrazole, an other object is the use of pyrazole for the preparation of 4-Fluoro-1H-pyrazole or salts thereof by means of fluorination reaction of pyrazole of formula (II).

DESCRIPTION OF EMBODIMENTS

Object of the present invention is a process for the preparation of 4-Fluoro-1H-pyrazole of formula (I) or salts thereof:

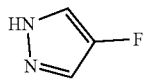

(I)

by reaction of pyrazole of formula (II):

(II)

with a fluorination reagent wherein said fluorination reagent is an electrophilic fluorination reagent.

The term electrophilic fluorinating reagent means a fluorinating reagent that is electrophilic, i.e. a fluorination reagent having a tendency to attract or acquire electrons.

It has been indeed surprisingly found that the reaction of 1H-pyrazole with an electrophilic fluorinating reagent provides selectively 4-Fluoro-1H-pyrazole. In other words, in the process of the invention, the electrophilic fluorination of 1H-pyrazole provides selectively 4-Fluoro-1H-pyrazole.

The electrophilic fluorination clearly differs from standard nucleophilic fluorination reactions, which do not provide at all 4-Fluoro-1H-pyrazole.

Thus, in the process of the invention, the electrophilic fluorination reaction of 1H-pyrazole provides 4-Fluoro-1H-pyrazole.

The term salts, includes hydrochloride, hydrobromide, sulphate, bisulphate, etc. of 4-Fluoro-1H-pyrazole, wherein the salt 4-Fluoro-1H-pyrazole hydrochloride is preferred.

According to an embodiment of the process, the reaction is carried out in presence of a base.

The term base, includes inorganic bases and organic bases.

According to a preferred embodiment of the process, the base is an inorganic base, since the inorganic bases provide better conversions compared with organic bases.

Examples of suitable inorganic bases are alkaline or alkaline hearty salts with weak acids.

In details, examples of inorganic bases are $NaHCO_3$, $Na_2CO_3$ or $Na_3PO_4$, $KHCO_3$, $K_2CO_3$ or $K_3PO_4$.

According to a preferred embodiment of the process, the inorganic base is $NaHCO_3$, $Na_2CO_3$ or $Na_3PO_4$, $KHCO_3$, $K_2CO_3$ or $K_3PO_4$.

According to a more preferred embodiment, the inorganic base is $NaHCO_3$ since it provides the best and fastest conversions compared with other inorganic bases.

According to a preferred embodiment of the process, the reaction is carried out at a pH value comprised in the range from 6 to 14 or, more preferably, from 6.0 to 8.0.

The electrophilic fluorinating reagent can be any fluorination reagent having a tendency to attract or acquire electrons, preferably, the electrophilic fluorination reagent is Fluorine gas or 1-chloromethyl-4-fluoro-1,4-diazoniabicyclo[2.2.2]octane bis(tetrafluoroborate) of formula (III):

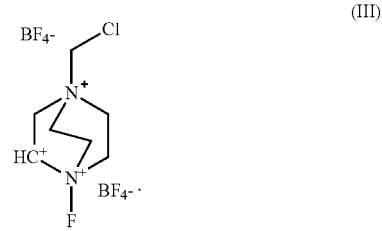

(III)

More preferably, electrophilic fluorination reagent is 1-chloromethyl fluoro-1,4-diazoniabicyclo[2.2.2]octane bis (tetrafluoroborate) of formula (III) since it does not requires special equipment such as those required for handling fluorine.

The reaction in the process of the invention can be carried out at a temperature comprised in the range from 20° C. to 80° C. or, preferably, from 50° C. to 80° C.

Preferably, the reaction is carried out at a temperature comprised in the range from 50° C. to 80° C. for a reaction time comprised in the range from 5 to 90 hours.

The reaction in the process of the invention can be carried out in an organic solvent, preferably in an organic solvent selected among acetonitrile, dichloromethane and mixtures thereof, more preferably the organic solvent is acetonitrile.

According to a preferred embodiment of the process, the reaction is carried out in an organic solvent being acetonitrile and in presence of $NaHCO_3$, since it provides the better and faster conversions, compared with the other inorganic bases and other solvents.

According to a more preferred embodiment of the process, the electrophilic fluorination reagent is 1-chloromethyl-4-fluoro-1,4-diazoniabicyclo[2.2.2]octane bis(tetrafluoroborate) of formula (III) and the reaction is carried out in an organic solvent being acetonitrile and in presence of $NaHCO_3$.

According to a preferred embodiment of the process, the reaction is carried out at a temperature comprised in the range from 50° C. to 80° C., the electrophilic fluorination reagent is 1-chloromethyl-4-fluoro-1,4-diazoniabicyclo [2.2.2]octane bis(tetrafluoroborate) of formula (III) and the reaction is carried out in an organic solvent and in presence of $NaHCO_3$, preferably the organic solvent being acetonitrile.

According to a preferred embodiment of the process, the reaction is carried out at a temperature comprised in the range from 50° C. to 80° C., the electrophilic fluorination reagent is 1-chloromethyl-4-fluoro-1,4-diazoniabicyclo [2.2.2]octane bis(tetrafluoroborate) of formula (III) and the reaction is carried out without the presence of any solvent and in presence of an inorganic base, preferably the inorganic base being $NaHCO_3$.

Alternatively and preferably, the reaction in the process of the invention can be carried out without the presence of any solvent, since the reaction can be carried out with pyrazole which is a reactant and liquid compounds, therefore also suitable as means to perform a reaction. Thus, the term "without the presence of any solvent" means only in presence of pyrazole, that acts as a solvent; or, alternatively, means that the reaction is carried out in pyrazole as means to perform said reaction. In such a case, the amount of pyrazole is in excess compared with the electrophilic fluorinating agent. In particular, the amount of pyrazole is comprise between 1 and 50 molecular equivalents compared to the electrophilic fluorinating agent, more preferable, from 2 to 10 molar equivalents, again more preferably from 3 to 6 molecular equivalents compared to the electrophilic fluorinating agent. In such a case, pyrazole acts both as a reactant and as mean or as solvent to perform the reaction.

Thus, according to a preferred embodiment of the process, the reaction is carried out without the presence of any solvent or the reaction is carried out in pyrazole as means to perform said reaction.

According to a more preferred embodiment of the process, the reaction is reaction is carried out without the presence of any base, i.e. the reaction is carried out without the addition of any additional base. Indeed, the excess of Pyrazole (II) compared to the compound of formula (III) acts as a base. Thus, the sentence "the reaction is reaction is carried out without the presence of any additional base" means that in the reaction that stoichiometric excess of pyrazole (II), compared to the compound of formula (III), acts as base.

According to a preferred embodiment of the invention, the amount of the pyrazole (II) is from 3 to 6 molecular equivalents compared to the compound of formula (III), more preferably from 4 to 5 molecular equivalents.

According to a preferred embodiment, the reaction is carried out without the presence of any solvent, without the presence of any additional base and the amount of the pyrazole (II) is from 3 to 6 molecular equivalents compared to the compound of formula (III), more preferably from 4 to 5 molecular equivalents.

According to a preferred embodiment, the reaction is carried without the presence of any solvent, without the presence of any additional base and the amount of the pyrazole (II) is from 3 to 6 molecular equivalents compared to the compound of formula (III), at a temperature comprised from 60° C. to 70° C., overnight.

In the process, the compound 4-Fluoro-1H-pyrazole of formula (I) can be extracted from the reaction mixture also comprising pyrazole of formula (II) by means of methyl-tert-butyl-ether (MTBE). It was indeed found that MTBE is well suitable, differently for other solvents (see example 5) to extract 4-Fluoropyrazole from a mixtures comprising pyrazole.

Further than MTBE, it was surprisingly found that the compound 4-Fluoro-1H-pyrazole of formula (I) can be extracted from the reaction mixture also comprising pyrazole of formula (II) with methyl-tert-butyl-ether (MTBE), wherein said extraction is carried out at pH=1.8 (see Table in Example 5). At such a specific value of pH, it is possible efficiently separate the compound (I) from the compound (II). Thus, both the combination of MTBE and the pH=1.8 provides a very unexpected effect of a very efficient separation of 4-Fluoro-pyrazole (I) from pyrazole (II). Such a separation is particularly important when the reaction is preformed without any other solvent, i.e. when an excess of pyrazole (II) is used as mean or solvent of the reaction.

An other object is the use of pyrazole of formula (II):

(II)

for the preparation of 4-Fluoro-1H-pyrazole of formula (I) or salts thereof:

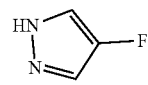

(I)

by means of fluorination reaction of pyrazole of formula (II).

According to a preferred embodiment, such a use is preferred wherein 1-chloromethyl-4-fluoro-1,4-diazoniabicyclo[2.2.2]octane bis (tetrafluoro borate) of formula (III) is employed as fluorination reagent.

The skilled in the art of organic chemistry can appreciate as the process of the invention allows a dramatic improvement, in terms of productivity, in the production of 4-Fluoro-1H-pyrazole or salts thereof considering the significant reduction in the number of synthetic steps, considering the fact that the starting material Pyrazole is a common and very cheap commodity and, considering that the industrial scale handling of a cancerogenic substance such as hydrazine is avoided.

EXPERIMENTAL SECTION

The starting material pyrazole is largely available on the market as well as all the other reagents. For Lab scale, they can be purchased by Sigma Aldrich Company.

Example 1: Preparation of 4-Fluoro-1H-pyrazole

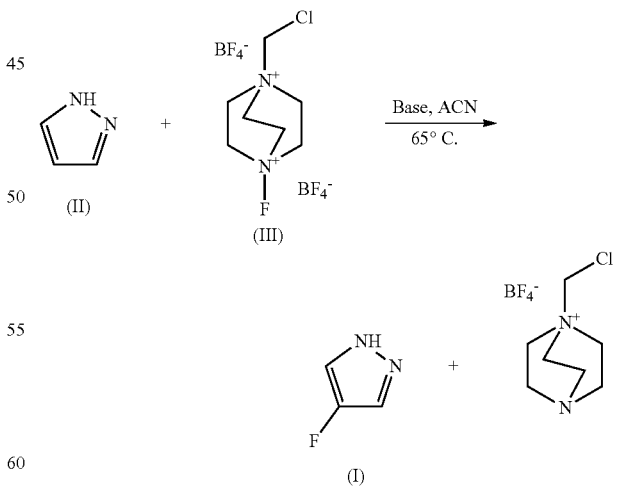

A 50 mL glass reactor was charged with 1 g of Pyrazole and 15 mL of acetonitrile and 1.04 g of 1-chloromethyl-4-fluoro-1,4-diazoniabicyclo[2.2.2]octane bis(tetrafluoroborate) of formula (III), then the mixture was stirred and heated to 65° C. for 1 hour.

Then 4.16 g of 1-chloromethyl-4-fluoro-1,4-diazoniabicyclo[2.2.2]octane bis(tetrafluoroborate) of formula (III) and 0.96 g of NaHCO₃ were added, both in 4 portions every 2 hours, keeping pH=6-7. Every portion comprises 1.04 g of compound of formula (III) and 0.24 g of NaHCO₃.

After the additions the reaction was continued for other 3 hours (overall reaction time=10 hours), then an In-process-control was performed with the following results:

GC Analysis: Pyrazole (II)=22.7% (A/A %), 4-Fluoropyrazole (I)=68.5% (A/A %);

Assay by HPLC provides 0.676 g of 4-Fluoropyrazole (I), i.e. a non-isolated molar yield of 4-Fluoropyrazole (I) of 53.5%.

Example 2: Preparation of 4-Fluoro-1H-pyrazole

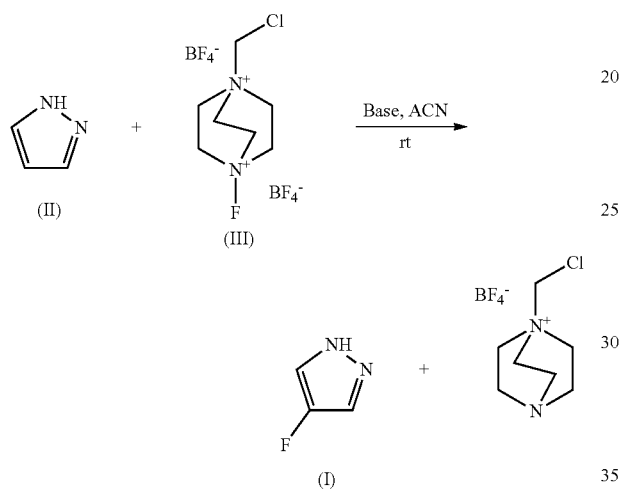

Example 1 was repeated but at room temperature instead of 65° C.

After 10 hours of reaction, an in-process-control showed the following results:

GC Analysis: Pyrazole (II)=92.98% (A/A % 4-Fluoropyrazole (I)=6.42% (A/A %).

Example 3: Preparation of 4-Fluoro-1H-pyrazole

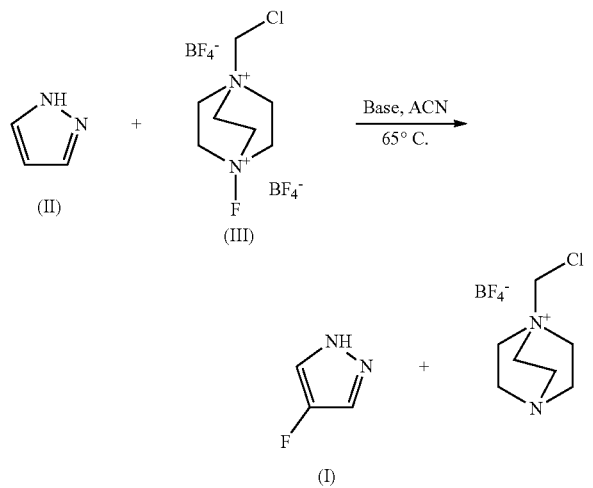

Example 1 was repeated but adding all the reagent at the start of the reaction.

After 10 hours of reaction an in-process-control showed the following results:

GC Analysis: Pyrazole (II)=29.62% (A/A %), 4-Fluoropyrazole (I)=59.08% (A/A %).

Example 4: Preparation of 4-Fluoro-1H-pyrazole—Process without Solvent and without Base or without any Additional Base

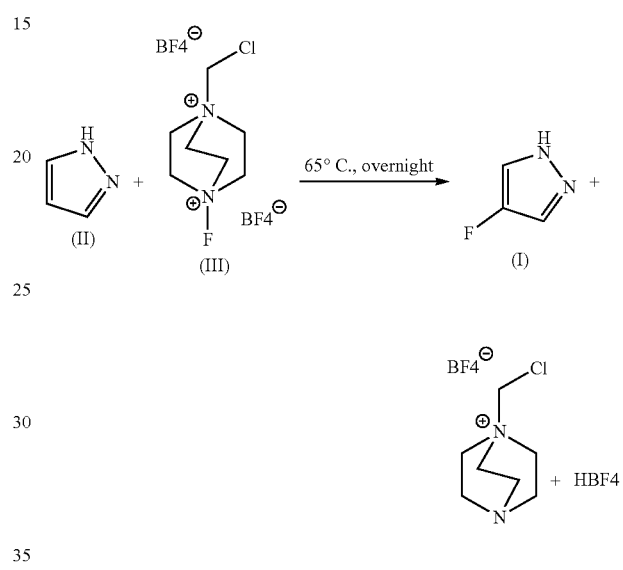

1 L glass reactor was charged with 384 g of pyrazole (II) (4.0 mol. Equivalents compared to the compound (III)) and heated to 75° C. to dissolution.

Then, the liquid was cooled down to 65° C. and then 500 g of 1-chloromethyl-4-fluoro-1,4-diazoniabicyclo[2.2.2]octane bis(tetrafluoroborate) of formula (III) were charged on portions.

The mixture was stirred at 65° C. overnight. An in process control showed that 80% of starting pyrazole was reacted. The reaction was stopped by cooling down the reaction mixture to room temperature.

When the mixture reached room temperature, 1 L of Methanol was added and then the suspension obtained was filtered to the remove the solid by-product of compound (III).

The filtrate (solution) was distilled to remove methanol. After the distillation was added dropwise HCl 36% to reach a pH of the mixture of 1.8.

The solution was then extracted three times with MTBE (the overall amount of MTBE was 12.5 Liters).

The organic layers where combined and then distilled to remove MTBE by distillation. After that, was charged HCl in MeOH solution (at least a stoichiometric amount of HCl compared to the pyrazole reactant), then distillate again to dryness. The was charged EtOAc for reslurry, and after filtering and drying, 95 g crude solid of 4-Fluoro-1H-pyrazole hydrochloride (abbreviated FPYR·HCl) were obtained, molar yield 54.9%, HPLC purity 89%, pyrazole 9.1%.

Example 4: Preparation of
4-Fluoro-1H-pyrazole—Process without Solvent
and without Additional Base—Study of the pH to
Extract 4-Fluoro-1H-pyrazole (FPYR) (I) with
MTBE

TABLE I

| pH study for MTBE extraction | |
| --- | --- |
| pH | FPYR (I)/pyrazole (II) in MTBE by GC |
| 2.5 | 1.74:1 |
| 2 | 4.19:1 |
| 1.9 | 5.7:1 |
| 1.8 | 8.86:1 |
| 1.7 | 15.63:1 (low yield) |

Other solvents such as $CH_2Cl_2$, Isopropyl acetate and sec-Butyl acetate were also tried to extract 4-Fluoro-1H-pyrazole (I) but none was better than MTBE.

What is claimed is:

1. Process for the preparation of 4-Fluoro-1 H-pyrazole of formula (I) or salts thereof:

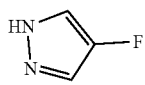

(I)

by reaction of pyrazole of formula (II):

(II)

with a fluorination reagent wherein said fluorination reagent is an electrophilic fluorination reagent, wherein the electrophilic fluorination reagent is Fluorine gas or 1-chloromethyl-4-fluoro-1,4-diazoniabicyclo[2.2.2]octane bis(tetrafluoroborate) of formula (III):

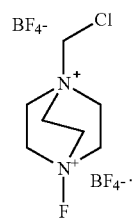

(III)

2. Process according to the claim 1, wherein the reaction is carried out in presence of a base or an inorganic base.

3. Process according to the claim 2, wherein the inorganic base is $NaHCO_3$, $Na_2CO_3$ or $NasPO_4$, $KHCO_3$, $K_2CO_3$ or $K_3PO_4$.

4. Process according to claim 1, wherein the reaction is carried out at a pH value comprised in the range from 6 to 14 or from 6.0 to 8.0.

5. Process according to claim 1, wherein the reaction is carried out at a temperature comprised in the range from 20° C. to 80° C. or from 50° C. to 80° C.

6. Process according to the claim 5, wherein the reaction is carried out at a temperature comprised in the range from 50° C. to 80° C. for a reaction time comprised in the range from 5 to 90 hours.

7. Process according to claim 1, wherein the reaction is carried out without the presence of any solvent or wherein the reaction is carried out in pyrazole as means to perform said reaction.

8. Process according to claim 1, wherein the reaction is carried out without the presence of any additional base.

9. Process according to claim 7, wherein the amount of the pyrazole (II) is from 3 to 6 molecular equivalents compared to the compound of formula (III).

10. Process according to claim 7, wherein the reaction is carried out without the presence of any solvent, without the presence of any additional base, and the amount of the pyrazole (II) is from 3 to 6 molecular equivalents compared to the compound of formula (III).

11. Process according to claim 7, wherein the reaction is carried out at a temperature comprised from 60° C. to 70° C., overnight.

12. Process according to claim 1, wherein 4-Fluoro-1H-pyrazole of formula (I) was extracted from the reaction mixture also comprising pyrazole of formula (II) by means of methyl-tert-butyl-ether (MTBE).

13. Process according to claim 12, wherein the extraction of 4-Fluoro-1H-pyrazole of formula (I) with methyl-tert-butyl-ether (MTBE) is carried out at pH=1.8.

* * * * *